United States Patent [19]

Pasque

[11] Patent Number: 5,423,821
[45] Date of Patent: Jun. 13, 1995

[54] STERNAL CLOSURE DEVICE

[76] Inventor: Michael K. Pasque, 13218 Hawkshead Ct., Town and Country, Mo. 63131

[21] Appl. No.: 181,827

[22] Filed: Jan. 18, 1994

[51] Int. Cl.$^6$ ............................................. A61B 17/56
[52] U.S. Cl. ................................... 606/74; 606/151; 606/228
[58] Field of Search ............... 606/228, 230, 231, 224, 606/226, 215, 216, 151, 157, 74, 232; 24/543, 503, 507, 136 L, 136 R, 94, 101 B, 113 MP; 206/63.3

[56] References Cited

U.S. PATENT DOCUMENTS

| | | | |
|---|---|---|---|
| 3,037,619 | 6/1962 | Stevans | 606/148 |
| 3,187,752 | 6/1965 | Glick | 606/231 |
| 4,034,763 | 7/1977 | Frazier | 606/226 |
| 4,730,615 | 3/1988 | Sutherland et al. | 128/335 |
| 4,750,492 | 6/1988 | Jacobs | 606/232 |
| 4,813,416 | 3/1989 | Pollak et al. | 128/335 |
| 4,880,002 | 11/1989 | MacGregor | 606/226 |
| 4,944,753 | 7/1990 | Burgess et al. | 623/16 |
| 5,078,731 | 1/1992 | Hayhurst | 606/232 |

FOREIGN PATENT DOCUMENTS 2132162 7/1984 United Kingdom .

OTHER PUBLICATIONS

Sirivella, S., et al., *J. Thorac. Cardiovasc. Surg.* 94: 591–95 (1987).
Kjaergard, H. K., et al., *Euro. J. Cardiothoracic Surg.* 6: 215–17 (1992).

*Primary Examiner*—Tamara L. Graysay
*Attorney, Agent, or Firm*—Patrick D. Kelly

[57] ABSTRACT

A surgical device and method are disclosed for closing the sternum following a median sternotomy. Instead of using stainless steel wire or a flat steel band, a strand of thin flexible suture material is used which is compressible in its radial dimension (either because of a hollow tubular shape, or due to solid material properties), while remaining strong and inelastic in its longitudinal dimension. The longitudinal strength may be maintained by using selected plastics, or by using nylon fibers or other materials for reinforcement. When not compressed, the strand has a diameter slightly larger than the diameter of the needle used to place the strand in position around the sternal halves, between the ribs. After insertion, the expandable suture material will provide gentle pressure against the surrounding tissue to minimize bleeding in the needle track. The soft suture material will also help cushion, distribute, and minimize the stresses and damage inflicted on the sternum or ribs during postoperative ambulation. A fastener device which provides additional advantages is also disclosed.

16 Claims, 4 Drawing Sheets

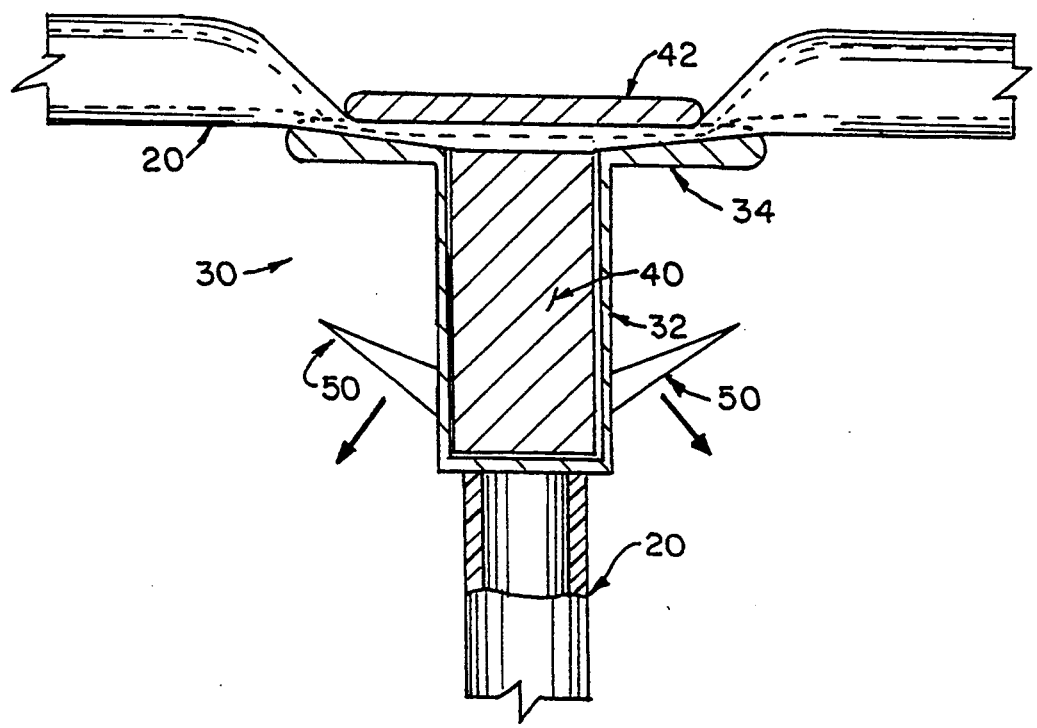
FIG. 8
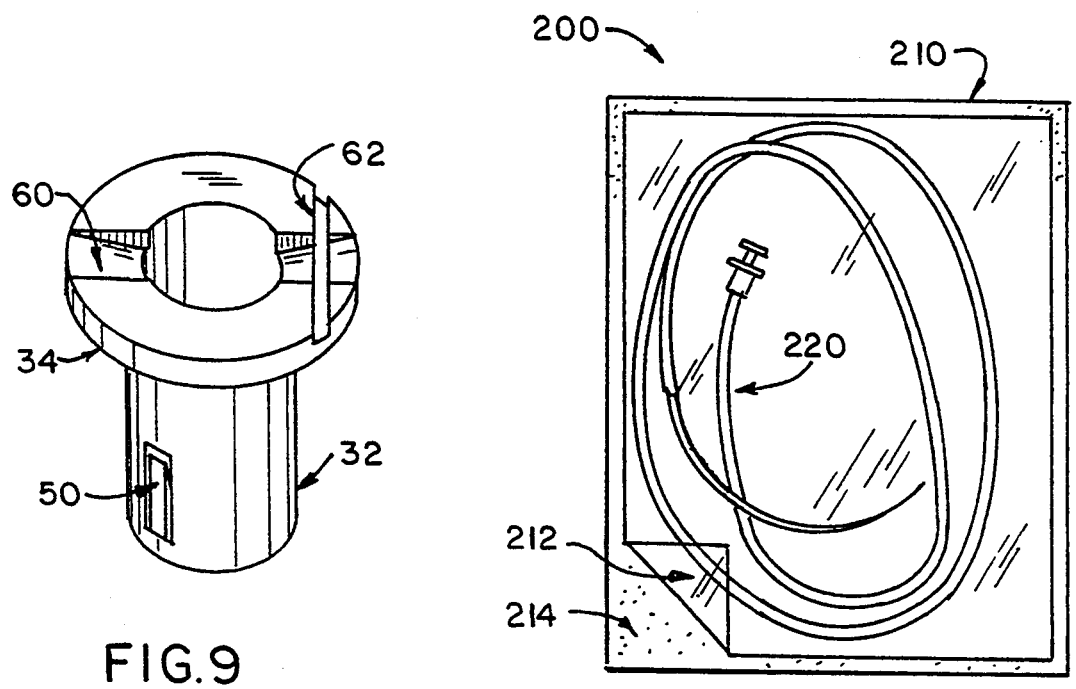
FIG. 9
FIG. 10

STERNAL CLOSURE DEVICE

RELATED APPLICATION

This application is related to U.S. application Ser. No. 07/967,146, filed on Oct. 27, 1992, now abandoned.

BACKGROUND OF THE INVENTION

This invention is in the field of surgical devices. It relates to surgery on the heart or lungs, and to other thoracic procedures that require opening of the sternum (the breast bone).

Most surgical procedures involving the heart or lungs are performed through a midline sternal incision, widely referred to as a "median sternotomy." The breast bone is comprised of the smaller manubrium superiorly (which is located near the neck) and the larger sternum inferiorly; the composite bone structure is usually referred to as the sternum. After an incision is made through the skin, the sternum is cut longitudinally using specialized power saws. The cut extends the entire length of the sternum, from the sternal notch, at the neck, to the xiphoid (the small protrusion of bone at the solar plexus). This midline cut allows the two halves of the sternum and the anterior portion of the ribcage to be spread several inches apart, giving the surgeons access to the heart and lungs. During surgery, the two halves of the sternum are held apart by mechanical retractors.

At the end of the surgery, the sternum must be closed, or "reapproximated." In the vast majority of cases, surgeons use stainless steel wire closure devices. These closure devices are composed of a thin stainless steel wire with a diameter of about 1-1.5 mm, coupled to a curved needle. The composite device is formed by inserting one end of the stainless steel wire into a hollow cavity in the non-sharpened end of the curved needle which is then crimped tightly to secure the wire to the needle. When this closure device is passed to the surgeon by a scrub nurse, the free end of the stainless steel wire is usually controlled by securing it with a small surgical clamp. The needle is used to pass the wire through the sternum or around the sternal halves, between the ribs that connect to the sternal halves at roughly right angles. The path of each of the six wires used for a typical sternal closure is as follows: 1) around and behind the left sternal half (between the ribs at each level) and 2) behind and up around the right sternal half (once again between the ribs at each level). In the upper portion of the closure, where the manubrium portion of the sternal bone is relatively wide, the needle is usually pushed through the bone. Below the manubrium, the needle is usually passed through "peristernal" tissue (i.e., tissue which surrounds the sternum) and usually does not penetrate the sternal bone except when the sternum is exceptionally wide.

After the wire is properly placed around the two sides using the needle, the needle is cut off and the wire is clamped at the cut end. This leaves a piece of wire that passes around and behind each of the sternal halves, with some excess wire attached to a clamp on each side of the sternum. This procedure is repeated until the desired number of wire segments (usually six) have been inserted into the peristernal tissue around the sternal halves. Each segment is usually positioned between two ribs, so that the wire does not have to penetrate the bones which constitute the ribs or the sternum (except at the wide manubrium).

After all of the wire segments have been properly positioned, the clamps of each wire are sequentially picked up by the surgeon and the wires are twisted around each other to secure them initially. The ends are then trimmed, and the twisted junctures are twisted again using a heavy needle driver, usually several more times, to create an extra-snug closure that will ensure that the sternal bones are pressed tightly against each other to minimize bleeding and ensure proper fusing of the sternal halves into an intact sternum to promote healing in a manner comparable to the healing of a broken bone.

Normally, the wire loops are left in place permanently. Unless problems arise which require a second surgical operation to remove the wires, they remain in place for the remainder of the patient's life, even after the sternal halves have fused together again.

Despite their widespread use, stainless steel wires can be highly problematic during surgery, and afterward. The problems associated with stainless steel wire closure of the sternum include:

1. The free end of a sternal wire can stab a surgeon, assistant, or scrub nurse during preparation or application. This problem is aggravated by the fact that the wire is typically cut using a wire cutter with relatively blunt blades, which generates a chiseled point which is typically quite sharp. To reduce the risk of stab wounds to surgeons and their assistants, which have become of major concern since the onset of the AIDS epidemic, clamps are used to secure the free ends of any wires in the patient's chest. Such clamps clutter the operating field, especially near the end of an operation, when at least a dozen clamps will be attached to the six wire loops; the clamps are tedious and time-consuming to work with and around, and even when they are properly attached to the wires, it is very common for exposed wire tips (or the clamps themselves) to tear surgical gloves and/or cause stab wounds. Such clamps may even promote operator injury, by holding the stiff wire in a fixed and unyielding position which the operator or assistants may brush against during the course of the operation. These sharp wire points and clamps expose the operating team to blood-borne diseases, including AIDS and hepatitis, and may break proper sterile technique and expose the patient to infection. Kjaergard et al, "Accidental Injuries and Blood Exposure to Cardiothoracic Surgical Teams," *European Journal of Cardio-Thoracic Surgery* 6: pages 215-217 (1992) reported that in a large study of cardiac surgical cases, stab wounds and glove lacerations caused by steel wires during sternal closure represented one of the most common causes of operator exposure to blood from a patient. Therefore, steel closure wires pose dangerous risks to cardiothoracic surgeons and their assistants, as well as to their patients.

2. The stiff, unyielding characteristic of stainless steel wire (compared to flexible plastics) make it unwieldy and difficult to manage on the operative field. After each wire is placed, the segment that sits below the sternal halves may press down on the heart or coronary artery bypass grafts while the other wires are being placed. Injury to these soft tissues can occur from these stiff wire segments during the normal course of sternal closure, further endangering the patient.

3. The wires are smaller in diameter than the needles that are used to pass the wires through or around the sternal halves. Thus, bleeding (supplied by the intercostal blood vessels or sternal marrow) often occurs in the needle tracks (i.e., the tunnels which are made when a needle passes through tissue or bone), since the diameter of the wire is not sufficient to press out in a radial manner to compress the small bleeding vessels. This results in unnecessary blood loss and visual obstruction of the operative field; occasionally, a return to the operating room becomes imperative to control internal hemorrhaging.

4. Postoperative stress on the closure loops may cause the thin wires to cut into and through the bone of the sternum. The result is further loosening of the sternal closure which can lead to painful instability of the two sternal halves with respiratory compromise and ultimately sternal dehiscence (i.e., complete separation of the sternal bones). Elderly patients or patients who have thin or highly porous bones (osteoporosis) are particularly susceptible to this complication. Instability of the sternal closure can also result in internal bleeding and can increase the risk of infection. If a second operation for sternal rewiring is required, it is made even more difficult by the fact that the sternal halves are often sliced into many pieces by the stainless steel wires.

5. Sternal wires occasionally break after an operation. Such breakage can be secondary to the thinning and deformation of the steel strand by the excessive torsion stresses that are sometimes applied to the loops during routine closure (especially as the operator twists the two ends tighter to effect a more secure approximation of the sternal halves). If a broken loop causes discomfort and/or protrudes toward or through the skin, a second surgical operation can be required to remove the wire.

6. For the rest of the patient's life, the stainless steel sternal wires interfere with any computerized axial tomography (CAT) or magnetic resonance imaging (MRI) scans of the chest. Unlike an X-ray, where steel loops generate clear and distinct images within a larger picture, steel closure loops can disrupt the entire image generated in a CAT or MRI scan.

Despite their obvious disadvantages, stainless steel closure wires are used in the overwhelming majority of the hundreds of thousands of median sternotomies performed each year. As described below, at least two efforts have been made to create better tools or techniques for sternal closure; however, neither of these modifications has succeeded in displacing stainless steel wires from their preeminent position in actual practice.

One prior art effort to create an improved sternal closure device is described in U.S. Pat. No. 4,730,615 (Sutherland and Vasconcellos, 1988). This patent describes a flat band made of metal and coated with plastic, which slides through a fastener device which was referred to in the patent as a buckle. The band contains protruding serrations (comparable to sawtooth projections which extend out from a flat surface) which interact in a ratcheting manner with an angled tang in the buckle. This allows the band to be pulled tight while the tang slides across the raised serrations. Subsequently, if tension is exerted which tries to expand or open the loop, the angled tang presses against the shoulder of a serration, thereby preventing the band from moving in the opposite direction. This holds the band in the tightened position.

This arrangement suffers from certain limitations; in particular, the sawtooth protrusions extending outward from the surface of the band can injure tissue as the band is being pulled through a patient's sternum or peristernal tissues. A modified closure device which avoided that specific problem is described in U.S. Pat. No. 4,813,416 (Pollak and Blasnik 1989), which described a flat stainless steel band with notches rather than serrations. The notches interact with bumps in a buckle device, to hold the band securely after the band it has been pulled tight. Except for the fact that they are made of steel, both of the foregoing devices are similar to various plastic bands that are widely used to bundle various types of merchandise, or to take up slack in electrical cords attached to household appliances.

These devices offer certain improvements over the standard sternal closure using wires; however, they suffer from various limitations which limit their utility. For example, the flat shape of these bands results in relatively sharp side edges, which can slice into the surrounding tissues or bone like a blade when they are pulled through behind the needle. These edges, if unprotected, also have considerable potential to slice into the fingers of the operating surgeon or assistants. In addition, both devices are made of stiff, unyielding metal which, just as in the case of stainless steel wires, makes the device unwieldy and capable of inflicting injury to the soft tissues below the sternum during closure.

It is also known, from anecdotal reports, that a number of cardiothoracic surgeons (including the Applicant) have tested various woven tapes, such as Mersilene tape, which is somewhat similar to a flattened shoe lace. Since this type of tape is relatively wide and flat, it helps to evenly distribute the stresses imposed on the sternal bone. As each loop is completed, the ends of the tape are usually tied together by hand.

In another field of prior art that is related only peripherally to sternal or other bone closures, various types of suture materials created for use in suturing soft tissues having certain types of surface porosity which encourage the growth of cells into the suture strands. For example, U.S. Pat. No. 4,034,763 (Frazier) teaches the use of sutures made of "woven or expanded" material in ligamentous joints or to repair Achilles tendons. The purposes of using "woven or expanded" material on the surface of the suture is to allow ingrowth of newly formed ligamentous tissues into the porous material. Such tissues can supplement and reinforce and may eventually replace the holding action of the suture.

One type of suture described by Frazier is hollow, to allow ingrowth of tissue. Although radial compressibility is not taught or mentioned by Frazier, his hollow suture would appear to be radially compressible, due to its hollow tubular structure and to the flexibility of the material used to make it. However, this type of suture would not resist such radial compression to any significant degree; if someone flattens or compresses it, it simply stays flat or compressed, like a piece of tubular cloth. Since these sutures do not try to return to their original diameter after compression, they would not provide a useful and gentle compressing action to minimize bleeding, as provided by the sutures described herein.

Another type of suture material with a porous outer surface was described in U.S. Pat. No. 4,880,002 (MacGregor). These sutures are made of an outer layer of permeable and compressible material, to promote cell growth into the suture material in a manner similar to the Frazier patent, surrounding an inner reinforcing strand. The sutures taught by MacGregor must also be longitudinally elastic (i.e., stretchable in the longitudinal direction). This longitudinal stretchability would render them unsuited for sternal closure use; as described below, sternal closure sutures must be substantially inelastic in the longitudinal dimension, to provide secure closure of sternal bones.

It should also be noted that sutures taught for other (i.e., non-sternal) purposes are much smaller in diameter than the sternal closure sutures described herein. For example, MacGregor teaches sutures which "typically" have diameters of about 1/20th of a millimeter or less; the largest suture size mentioned by MacGregor is a USP size 2 suture, which has a diameter of about 0.6 mm, but even that is too thin to use as sternal closure material, since it would pose a grave risk of wearing and cutting through the sternal bones of the patient. By contrast, sternal closure sutures preferably should have a thickness of at least about 2 mm.

The Applicant has created a sternal closure device and method which differ substantially from any known items of prior art, and which offer a number of advantages not available from the prior art. The subject invention uses a thin, flexible suture material which has a circular cross-section, such as a clear, soft plastic which is strong and inelastic in its longitudinal dimension while remaining soft and compressible in its radial dimension. The suture remains compressible in its radial dimension because of its hollow tubular shape; alternately, it can be composed of a radially compressible soft spongy material, reinforced by a stronger material such as nylon fibers.

When not compressed, this suture material should have a diameter slightly larger than the diameter of the needle used to insert the suture through the sternal bone or peristernal tissue. Unlike a stainless steel wire or band, this suture material will expand gently in the radial direction after insertion, thereby creating gentle pressure against the surrounding tissue. This causes the suture material to act as a compress to minimize bleeding in the needle track.

In addition, unlike a steel wire or band, this type of suture material will help cushion, distribute, and minimize the torsion and other stresses that are inflicted on the sternal bones during normal post-operative ambulation. These advantages can be obtained with no loss of longitudinal strength by using selected materials such as polyvinyl chloride, or by using an internal material with high tensile strength such as nylon to reinforce a soft material.

In addition to the advantages which arise from the selection and design of the suture material, this invention also discloses a fastener device which provides additional advantages described below.

Accordingly, one object of this invention is to provide a sternal closure device which uses a strand of flexible material which can be radially compressed and which is slightly thicker than the needle used to insert the strand through the sternal bone or peristernal tissue, so that after insertion, the material will expand gently and provide mild pressure against the surrounding tissue, to minimize bleeding.

Another object of this invention is to provide sternal closure suture material having a relatively thick and preferably round cross-section which does not have any thin or squared edges or thin-diameter cross-sections, which therefore evenly distributes stresses and minimizes injury to bone or tissue surfaces that contact the suture material.

A third object of this invention is to disclose a sternal suture fastener device which offers an improved gripping component for securing the suture material.

These and other advantages will become apparent from the following summary and detailed description of the invention and from the accompanying drawings.

SUMMARY OF THE INVENTION

A surgical device and method are disclosed for closing the sternum following a median sternotomy. Instead of using stainless steel wire or a flat steel band, a strand of thin flexible suture material is used which is compressible in its radial dimension (either because of a hollow tubular shape, or due to solid material properties), while remaining strong and inelastic in its longitudinal dimension. The longitudinal strength may be maintained by using selected plastics, or by using nylon fibers or other materials for reinforcement. When not compressed, the strand has a diameter slightly larger than the diameter of the needle used to place the strand in position around the sternal halves, between the ribs. After insertion, the expandable suture material will provide gentle pressure against the surrounding tissue to minimize bleeding in the needle track. The soft suture material will also help cushion, distribute, and minimize the stresses and damage inflicted on the sternum or ribs during postoperative ambulation. A fastener device which provides additional advantages is also disclosed.

BRIEF DESCRIPTION OF THE FIGURES

FIG. 8 is a side view of a fastener device in the closed position, showing the fixation prongs in the extended position.

FIG. 9 is a perspective view of the cylinder and base of the fastener device.

FIG. 10 depicts a needle, suture, and fastener assembly enclosed within a sterile package.

DESCRIPTION OF THE PREFERRED EMBODIMENTS

Figure 1:
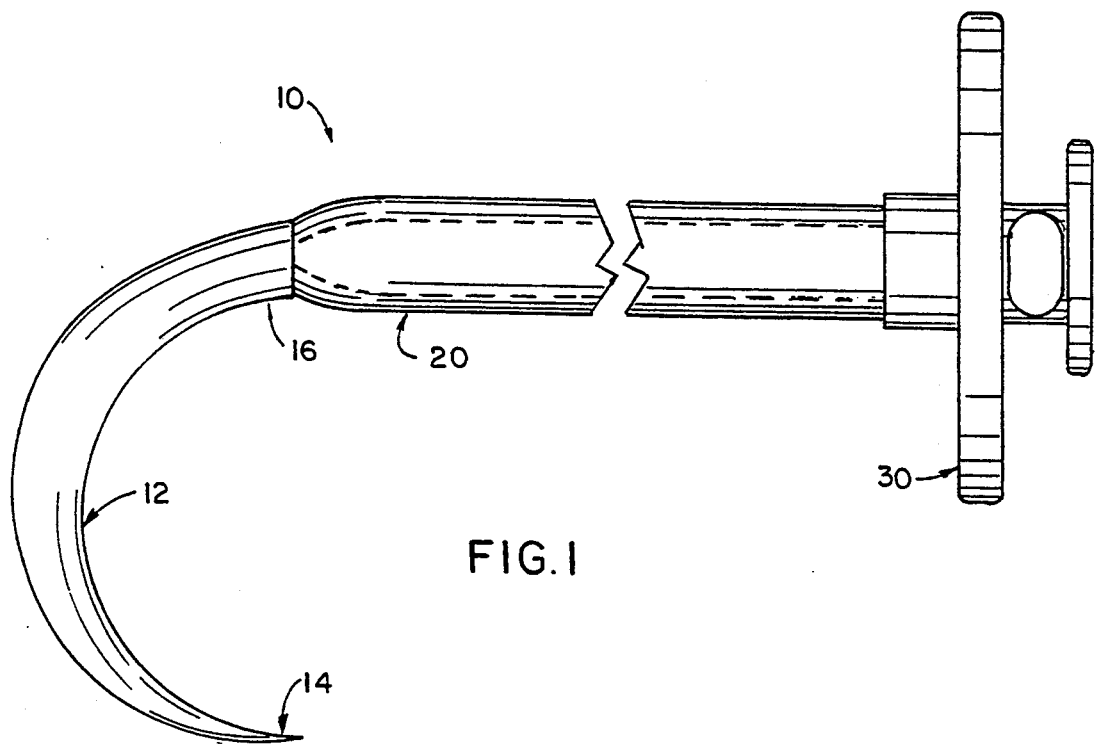
FIG. 1 depicts the flexible strand of this invention coupled to a curved needle at one end, and to a securing device at the other end.

Referring to the drawings, number 10 in FIG. 1 refers to a sternal closure assembly comprising a curved needle 12, a compressible suture strand 20, and a suture strand fastener device 30. This assembly can be used to close the sternum following a median sternotomy. It can also be used following any other type of thoracic operation which involves cutting the sternal bone into two or more divided segments, or to repair a sternum which has been broken due to accidental injury or other causes.

The curved needle 12 can be a conventional sternal needle, which typically has a semi-circular shape, made of suitably hard metal alloy such as stainless steel. Conventional sternal needles have a sharpened proximal end 14 and a hollowed-out tubular structure 16 at the distal end which allows attachment to the suture material. In prior art needles attached to stainless steel wires, the cylindrical wall of the tubular structure 16 is crimped around the wire, as described in the Background section. Such needles can be readily adapted to this invention by inserting one end of the suture strand 20 into tubular end 16, and crimping the tubular end 16 around the flexible strand. The needle diameter, typically about 1.25 millimeters (mm) for conventional sternal closures, should be significantly smaller than the diameter of the suture strand when the suture is relaxed and fully expanded. A suitable suture material, when relaxed, should have a diameter in the range of about 2 to about 3 mm if used with a 1.25 mm needle.

The attachment of suture strand 20 to needle 12 does not need to be excessively strong; it comes into play only after the needle has been pushed through the bone or tissue, as the needle pulls the strand through the needle track. The needle will be cut off after the loop has been created, so the mode of attachment of the suture strand 20 to needle 12 will have no bearing on what happens after an operation is completed. Accordingly, any suitable attachment means, such as biocompatible glue, can be used. Alternately, if a suture material is used which has a flexible coating surrounding a reinforcing strand, the porous coating can be stripped off of a short length of the reinforcing strand, and the reinforcing strand can be passed through the eye of a needle.

The suture strand 20 is made of a radially compressible material. This feature allows the suture material to pass through the narrow needle track caused by passage of the narrower sternal needle. The suture material thereby expands slightly in the track after placement. This creates gentle pressure against the tissue which surrounds the needle track. This gentle pressure minimizes bleeding, in a manner similar to a compress or tamponade. By contrast, when stainless steel wires are used for sternal closure, the wire is smaller in diameter than the needle which made the hole. Therefore, any bleeding source which the needle passed through remains free to bleed; unlike the sutures of the subject invention, steel wires do nothing to help suppress or control such bleeding.

Despite its radial compressibility, the suture must have a high level of longitudinal strength, and a low level of longitudinal yield; it must not stretch a substantial amount when subjected to tensile forces of the magnitude that are generated during post-operative ambulation. Otherwise, it would not be able to hold the two halves of the sternum tightly enough to promote proper healing of the bone. Any slippage of the two bone segments relative to each other when they are in a state of partial healing would act, in effect, as a new break in the bone; it would delay and prolong the healing process, and it could lead to misalignment of the sternal halves when they fuse together again. This requirement apparently is the primary reason why stainless steel wires are used in the vast majority of sternal closures. Steel wires suffer from numerous problems, but they have one thing in their favor: they will not stretch longitudinally during post-operative ambulation. That factor apparently has been sufficient to ensure their widespread use despite their dangers and disadvantages.

Figures 2, 3, 4:
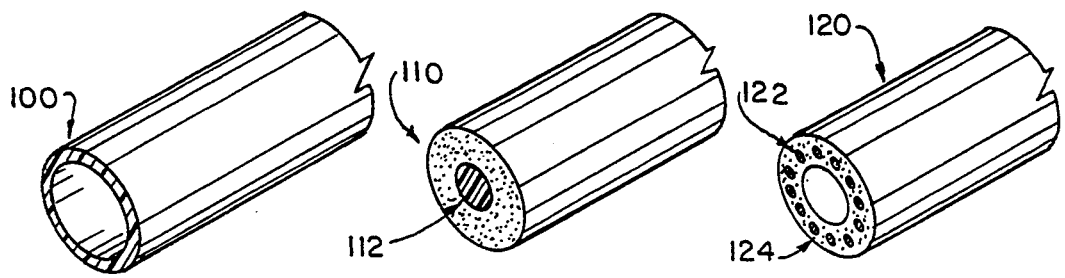
FIGS. 2, 3, and 4 depict three types of radially compressible suture material.
Figure 5:
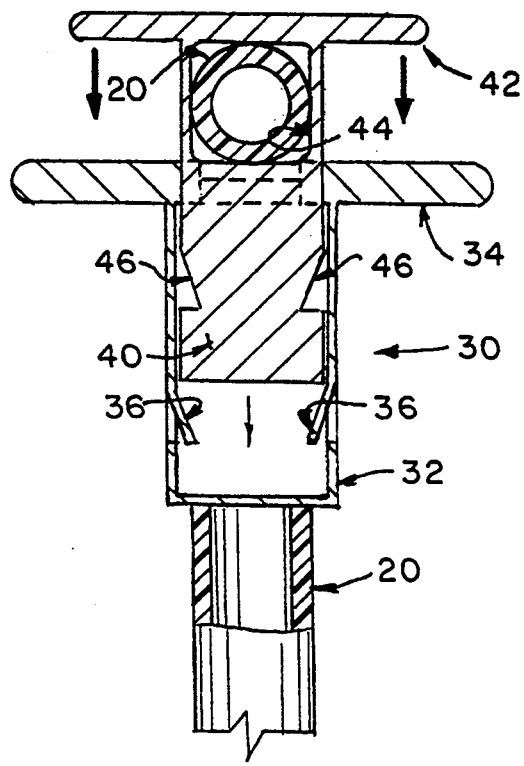
FIG. 5 is a cross-sectional side view of a fastener device in the open position, showing a suture (in cross-section) passing through an orifice in the fastener.

However, several other types of material can be used to provide sternal sutures having a desired level of flexibility and radial compressibility without sacrificing longitudinal strength, if they are properly designed. For example, a hollow tube 100, shown in FIG. 2, made of polyvinyl chloride or other flexible plastic and having an external diameter in the range of about 2 to 3 mm can be used. Alternately, a pliable material 110 having a moderately dense foam structure can be coated onto the outside of an internal single- or multi-filament strand of material 112 such as nylon or polypropylene, as shown in FIG. 3. As another alternative, a hollow reinforcing tube 120 can be provided by strands of strong fibers 122, such as nylon, woven in a manner comparable to the external shielding in a coaxial cable or a reinforced hose; these reinforcing strands 122 can be impregnated with, or coated by, a second material 124 having foam-like or other flexible characteristics, as shown in FIG. 4. In a similar fashion, the wall of the hollow soft plastic tube shown in FIG. 2 can be supported by nylon or other reinforcing strands as demonstrated in FIG. 4 to improve longitudinal strength. The accumulation of blood or other tissue inside these tubular structures is unlikely since in practice they will be closed at both ends by the method of their application.

These approaches can be used to create sutures which will not stretch or yield significantly in the longitudinal direction, but which are radially compressible. It is also likely that similar results could be achieved using specially designed polymers having controlled molecular structures which can be stretched or compressed in one direction but not the other; however, the designs discussed above can be carried out using relatively inexpensive starting materials.

A numerical value for the acceptable limits of longitudinal yield (which can be expressed as a modulus of elasticity) can be generated, if desired, by evaluating materials such as Mersilene tape, which has sufficiently low elasticity to render it useful for sternal closure. To provide an approximation, it is anticipated that suture material which stretches less than about 2 to 3 percent (i.e., less than about 2 or 3 mm per 10 cm length) when subjected to a 5 kilogram load is sufficiently inelastic to render it suitable for use as described herein.

Various flexible biocompatible materials have been developed which are good candidates for use as sternal closure sutures as described herein. Non-absorbable materials include plastics such as polyvinyl chloride and other polymers, and fabrics sold under trademarks such as DACRON and GORETEX. It is also possible to use absorbable sutures if they provide sufficient tensile strength (which is a function of suture diameter as well as the material used); candidate materials which are currently used as absorbable sutures include polygalactin (sold under trademarks such as VICRYL) and polyglycolic acid (sold under trademarks such as DEXON).

During sternal closure, near the completion of open-chest surgery, a needle 12 attached to a suture strand 20 is passed through or around the sternal halves, drawing the suture strand 20 into position. Under routine circumstances, the needle initially penetrates the anterior chest wall either through or around the left side of the sternum, between each set of ribs as they approach the sternum at roughly right angles. It emerges beneath the left sternal half into the midline incision which was used to separate left and right sternal halves. It is then passed through below and around the right side of the sternum, and it emerges on the right side of the sternum where it exits the chest wall.

The round cross-section and the compressibility of a suture strand 20 will help it pass smoothly and atraumatically through peristernal tissue, and through any bone which is penetrated. To make insertion even easier, the suture strand (or selected suture strands, such as specific strands which will pass through the manubrium) can be lubricated by a low-friction coating such as polytetrafluoroethylene (PTFE, sold under the trademark TEFLON) or by a biologically absorbable gel or fluid which would function as a lubricant. Such suture coatings are taught in, for example, U.S. Pat. No. 3,187,752 (Glick).

After the initial placement is completed for all of the suture strands, the operative team usually checks the underside of each sternal half to see how much bleeding is coming through the suture holes. With stainless steel wires, there typically are multiple bleeding sources including intercostal or internal mammary arteries and veins and sternal marrow. Since steel wires are smaller in diameter than the needles used to place them, any tissue which is bleeding due to needle damage remains free to bleed until clot formation eventually stops the bleeding or other measures are taken by the surgeon to stop the bleeding. By contrast, in the subject invention, the tubular suture has a larger diameter than the needle, and expands against the tissue which surrounds the needle track. This compresses and tamponades any bleeding source.

It should also be noted that the tubular sutures used herein do not have relatively sharp side edges, which are a problem with steel bands having flat cross-sections, disclosed in U.S. Pat. Nos. 4,813,416 and 4,730,615 (summarized above). The sharp side edges of flat steel bands are likely to cut through tissue lying along the sides of the bands, causing increased tissue trauma and bleeding. In addition, the spine modification described in U.S. Pat. No. 4,730,615 has protruding serrations that must be pulled through the peristernal tissue, causing frank tissue disruption and aggravated bleeding. That is not a problem in the subject invention; the needles and suture surfaces are completely smooth. In addition, the soft and compliant suture strands used herein are much easier to handle than steel wires or bands, and because of their flexible characteristics, they are much less likely to injure cardiac or vascular structures beneath or around the sternal halves during or after closure.

It should also be noted that the needle is cut off immediately after encircling the sternum and passing it through the orifice 44 in the plunger 40 of the fastener device 30. There are, therefore, no exposed sharp wire ends, which can cut or tear surgical gloves or injure any of the operative team when steel wires are used. This invention thereby avoids a significant risk of transmission of blood-borne infections.

In addition, it is not necessary to secure the ends of the multiple suture strands with surgical clamps after the strands have been placed in their initial position, before final tightening and closure. Therefore, the multiple clamps which normally lay in the surgical field when stainless steel wires are used are not necessary in this invention and will not clutter the operative field or cut the gloves or fingers of the operative team.

If desired, an alternative method can be used to insert the suture strands around the sternal halves without using a sternal closure needle. In this alternative method, a tool such as a hemostat or needle-nosed clamp is inserted through the intercostal (between the ribs) space on the anterior chest wall just lateral to the left sternal half and into the patient's chest beneath the left half of the sternal bone. A surgeon holding the end of the suture strand with another needle-nosed clamp inserts the end of the suture into the patient's chest through the midline incision. It is then grasped by the needle-nosed clamp which was inserted through the intercostal muscle. The clamp is then withdrawn, thereby drawing the suture strand around the left sternal half. This procedure is then repeated by inserting the other end of the suture into the midline incision and beneath the right half of the sternum, so it can be grasped and drawn through by a clamp inserted in a similar manner through the intercostal space on the right side of the sternum.

The Fastener Device

If desired, the sternal closure strands can be secured into loops, after emplacement, by tying the two ends of a strand in a conventional manner. Alternately, a loop can be closed using a free-standing attachment device such as the clip shown in U.S. Pat. No. 5,078,731 (Hayhurst).

In an alternate preferred embodiment, a fastener device 30 shown in FIGS. 5 through 8 can be coupled to the distal end of the suture 20. The bottom end of cylinder component 32 is permanently secured to the end of suture strand 20 by means such as a biocompatible glue. The top end of the cylinder 32 is firmly attached to a relatively flat component, referred to herein as the fastener base 34. Cylinder 32 encloses a plunger 40 which is attached to a plunger cap 42. An orifice 44 passes through the shaft of plunger 40.

When the needle has completed its path during insertion of a suture strand, the suture strand 20 is drawn all the way through, until the fastener base 34 of the fastener 30 (which is attached to the distal end of the suture 20) seats firmly against the anterior surface of the sternum or peristernal tissues. This leaves the cylinder 32 embedded in the sternal or peristernal tissues. The size and shape of the fastener 30 prevents it from being pulled all the way through the sternum or soft peristernal tissue.

In a normal sternal closure, six sutures are used; each suture is positioned between two ribs. All six suture pieces are placed in the proper initial position, circling around and behind the sternum. The needle is passed through the orifice 44 in the plunger 40 of the fastener device 30 that is attached to that suture, thereby drawing the suture through the orifice. This closes the sternal closure loop, and the needle should be cut off as soon as possible, to eliminate any risk of inadvertent stab wounds. The fastener orifice 44 preferably should be slightly smaller in diameter than the suture strand; this will allow it to temporarily hold the suture strand in place while the other sutures are placed. The suture is left long enough to allow easy manipulation of the two sternal halves as the rest of the sternal sutures are placed.

Figure 6:
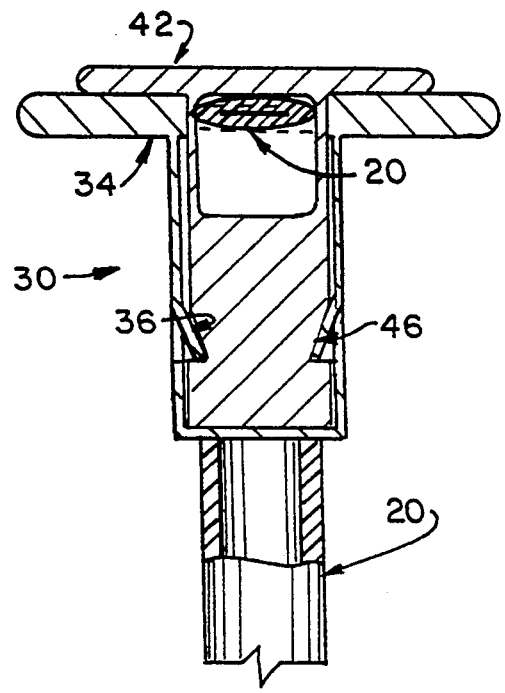
FIG. 6 is a cross-sectional side view of a fastener in the closed position, showing the suture strand crimped and held securely in place.

When the initial placement steps are completed for all of the suture strands, the tightening procedure is ready to begin. For each suture strand, the free end 25 of the suture strand 20 is inserted through the fastener orifice 44 if this has not already been performed as each individual suture was placed. This orifice 44 passes through the plunger 40. When a suture strand has been tightened to a desired tension, the plunger 40 is pushed down. This squeezes and tightly crimps the suture strand 20 between the roof of orifice 44 and the surface of fastener base 34, as shown in FIG. 6 (along the axis of suture strand 20) and FIG. 8 (perpendicular to suture strand 20). The plunger 40 is held in the crimped position, tightly gripping the suture 20, by means of two locking devices 36 mounted inside the barrel of cylinder 32. These locking devices 36 engage accommodating slots 46 in the sides of plunger 40. The plunger 40 and/or the cylinder 32 are made of a slightly deformable plastic, allowing the plunger to be pressed down despite the resistance generated by the locking devices 36.

Figure 11:
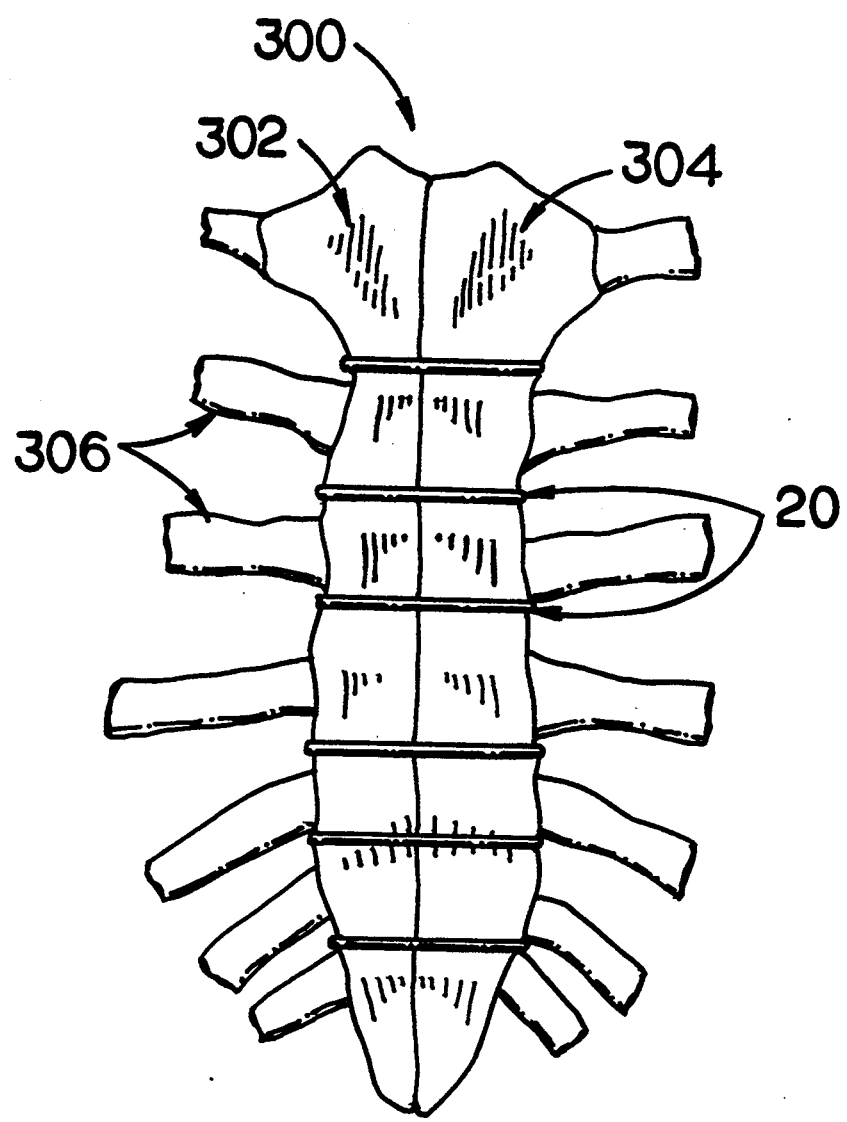
FIG. 11 schematically depicts the suture strands of this invention emplaced around a sternum.

FIG. 11 illustrates a plurality of suture strands 20 that have been emplaced around a sternal bone 300, which was divided into halves 302 and 304 during open-chest surgery. As shown, each strand 20 is positioned between adjacent ribs 306.

Figure 7:
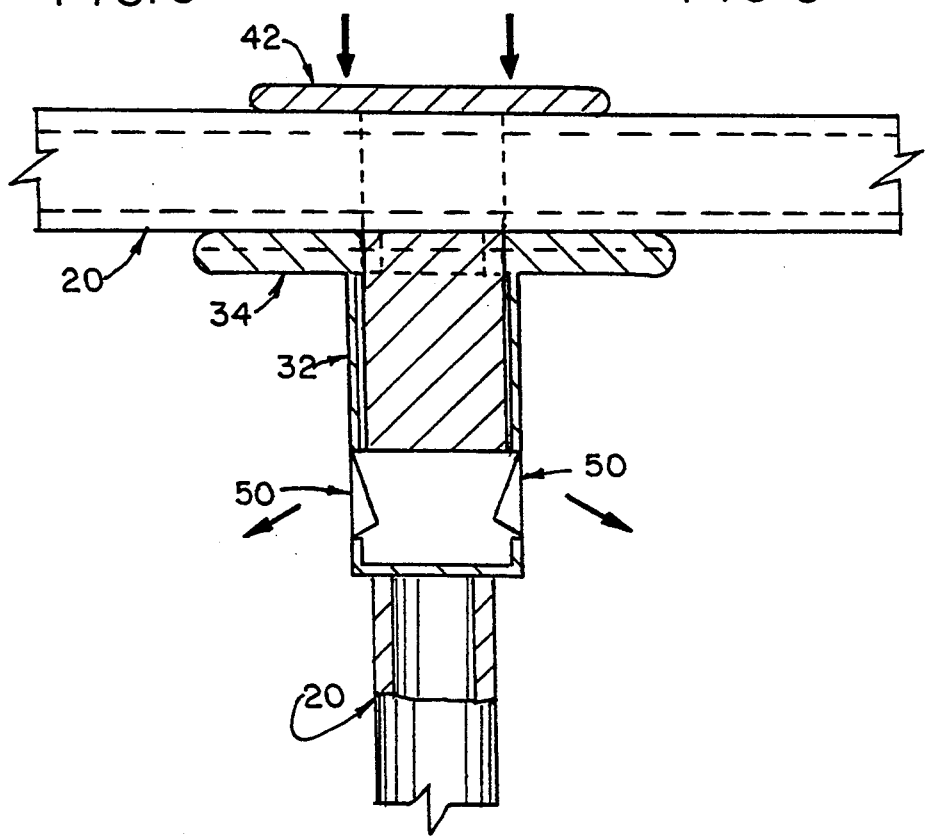
FIG. 7 is a different side view of a fastener device in an open position, showing two extendible fixation prongs which will secure the fastener in the soft tissues adjacent to the sternum and prevent migration of the suture and fastener around the sternum.

If desired, the cylinder barrel 32 can also be fitted with one or more extendable fixation prongs 50, shown in FIGS. 7 and 8. Before plunger 40 is pushed down, fixation prongs 50 are in a retracted position, as shown in FIG. 7, and are coupled to the cylinder barrel 32 by means of pivoting attachments 52 at or near the lower end of the cylinder barrel 32. These pivoting attachment points can be provided by mechanical hinges, or by thin deformable plastic junctures between the cylinder barrel and the fixation prongs. When the plunger 40 is pushed downward, the plunger presses against the sloped upper region of the fixation prongs, which pushes the fixation prongs in an outward direction, into the soft peristernal tissue as shown in FIG. 8. This causes the fixation prongs to secure and stabilize the position of the fastener device 30 in the peristernal tissue. The extended prongs prevent outward migration of the fastener 30 around the sternum, along the path of the suture loop, while the fastener base 34 prevents migration into the chest cavity. The fastener device therefore remains seated next to the sternum, typically on the patient's left side, nestled unobtrusively between two ribs.

By contrast, conventional stainless steel wire closures, and the prior art banding devices disclosed in U.S. Pat. Nos. 4,813,416 and 4,730,615 do not have any comparable method for preventing migration of the fixation device. The result is that the wire twist-closure, the "buckle" described in U.S. Pat. No. 4,813,416, or the "head" described in U.S. Pat. No. 4,730,615 can migrate around the sternal bone. Usually, migration tends to bring the wire loop closure devices to an anterior position and places them on top of the front of the sternum, where they may become annoying and can cause discomfort, and occasionally require corrective surgery.

The fastener device 30 should have a size which is as small as possible consistent with its function and with the need for direct handling by surgeons wearing surgical gloves. For example, the fastener base 34 should have a diameter of less than about 1 cm; a diameter of about 5 or 6 mm is preferred for use with sutures having diameters up to about 3 mm. The height from cap to barrel end when the plunger is depressed, should also be less than 1 cm and preferably should be in the range of about 5 to 7 mm.

In addition, FIG. 9 shows two enhancements in the fastener base 34 which can be used to further reduce the profile of the fastener after implantation. A groove 60 which accommodates the suture strand 20 will allow the suture strand to be compressed to a very low profile when the fastener is in the closed (crimping) position; this low suture profile is indicated in FIGS. 6 and 8. If desired, the surface of the groove (and the top surface of the plunger orifice 44) can be serrated slightly or otherwise provided with a rough surface, to improve their ability to grip the suture material without slippage. In addition, a second groove 62 can be provided in the top of the fastener base 34. After closure, this second groove will serve as a cutting guide to help the surgeon trim the free end of the suture strand.

If desired, the fastener device can be provided with a means for releasing the plunger after it has been depressed, in case the length of the suture needs to be adjusted. One way to allow such release would be to provide ramps on the sides of the slots 46 which hold the locking members 36. These would allow rotation of the plunger 40 relative to the cylinder 32, to release the locking members 36. This would not create a substantial danger of spontaneous release, since the suture strand sitting in groove 60 will resist any such rotation.

The fastener design described above is only one possible design; other fastener configurations could be used so long as they allow effective sternal closure. For example, a fastener device could be provided with two separate orifices, or with a single orifice wide enough to hold two suture strands side-by-side. If such fasteners were used, they would not need to be affixed to one end of the suture strand, and a single sternal needle coupled to a single long piece of suture material would be sufficient to close the entire sternum if six fastener devices were enclosed in the sterile pouch holding the needle and suture strand.

After all of the sutures have been tightened, secured, and trimmed, the fascial closure is performed in the usual manner, to cover the devices completely, then subcutaneous and skin closure is carried out using a conventional routine.

Routine postoperative care of cardiothoracic patients requires aggressive pulmonary rehabilitation including early ambulation. The coughing, deep breathing and movement required to attain these goals imposes substantial stresses on the sternal closure. In conventional sternal closures, this results in tension of the stainless steel wires against the bone of the sternum. The end result, particularly in patients who are elderly or who suffer from osteoporosis or other degeneration of the sternum, is that the narrow stainless steel wires can cut through the bone. This loosens the sternal approximation, and leads to undesired movement of the sternal halves against the wires. This often leads to increased incisional pain, and in the some cases to complete sternal separation and/or sternal infection. These catastrophic complications often mandate further surgery in an attempt to secure the sternal closure.

The subject invention will lessen the chance of these complications. The suture materials described herein allow more than enough longitudinal strength with minimal longitudinal deformation, thereby allowing firm fixation of the sternal halves. At the same time, the increased diameter of the sutures described herein, compared to conventional stainless steel wires, allow any tensile stresses to be evenly distributed across a larger area, which decreases the chances of the sutures cutting into the sternal bone and loosening the sternal approximation. In addition, even when sternal healing takes place with a stainless steel wire closure, some of the wires may break (which can occur years after the original operation), and the sharp ends of the broken wire can injure internal tissue and protrude through or against the skin requiring another surgical procedure to remove them. Most such wire breaks occur where a wire has been twisted, since twisting of a steel wire weakens the wire. This weakening effect does not arise with the compliant suture material as described herein, and there is little or no danger of suture breakage under the subject invention. In addition, even if a suture described herein were to break, the free end would not protrude into the surrounding tissues.

Articles of Manufacture

In addition to a surgical method, this invention also discloses an article of manufacture comprising a needle, a radially compressible suture strand as described above, and a fastener, wherein the needle and the fastener are coupled to the ends of the suture strand.

In addition, this invention also discloses a kit which includes one or more needle/suture/fastener assemblies which are contained inside a sealed package which maintains the sterility of the assembly. A preferred kit could include a single assembly; alternately, it can include several (such as three or six) assemblies.

This article of manufacture 200 is depicted in FIG. 10. In this drawing, packaging device 210 contains a needle, suture, and fastener assembly 220. The package 210 preferably is an airtight, watertight sealed plastic pouch. A transparent front layer 212 (which is shown partially opened at one corner, for illustration purposes) enables the user to quickly identify or confirm the contents. Until the package is opened, the front layer 212 is sealed around the entire periphery of the package to a back layer 214, which can be either opaque or transparent. The two sealed layers form a relatively flat envelope which is impervious to water, air, bacteria, and viruses. Most sterile kits intended for use during surgery are actually double-sealed; they have an external sealed pouch which keeps out dirt, and an internal sealed pouch as well. As soon as the outside pouch is opened, the internal pouch is removed, positioned over a sterile table in the operating room, and cut open so that the contents spill out, without being touched, onto the sterile table.

An alternative preferred article of manufacture comprises a sternal closure needle (which preferably should be semi-circular in shape) coupled to a radially compressible suture material, wherein the needle and suture assembly is enclosed within a sealed sterilized package. As described above, the suture material can be coupled together by means of fastener devices which are not initially attached to the suture material, or by tying two free ends together.

Yet another article of manufacture which is disclosed by the subject invention comprises a suture strand as described herein, enclosed within a sealed sterilized package. As mentioned above, a suture strand can be positioned around and behind the sternal halves following a median sternotomy using tools such as a hemostat or needle-nosed clamp. Although this placement means is not preferred, it is entirely feasible. Accordingly, this invention discloses a suture material having radial compressibility but little or no longitudinal yield, enclosed within a sealed and sterilized package, without requiring that a sternal closure needle must be coupled to the suture strand.

Any type of packaging material which is conventionally used to store sterile surgical instruments or devices can be used, such as plastic which is permeable to a sterilizing gas such as ethylene oxide, or plastic which will withstand the temperatures used in autoclaves. The packaging material and enclosed items can be sterilized in any manner suitable to render the enclosed items safe for use during surgery, such as by means of ethylene oxide, by high temperature, or by ionizing radiation, provided that the method used will not seriously degrade the strength of the suture material or any fastener devices. After sterilization, the sealed package will maintain the sterility of the enclosed items even if the outside of the package becomes soiled.

Thus, there has been shown and described an improved device and method for closing a sternum following a median sternotomy, which fulfills all the objects and advantages set forth above. It will be apparent to those skilled in the art that various changes and modifications to the specific embodiments described herein are possible. Any such changes that do not depart from the spirit and scope of the invention are deemed to be covered by the invention, which is limited only by the claims which follow.

I claim:

1. A method of surgically reapproximating a sternal bone which has been divided into two or more segments, comprising the following steps:
   a. providing a surgical needle and a radially compressible suture strand which is firmly coupled to the needle, wherein the needle has a size and shape suitable for positioning the suture strand around a sternal bone that has been divided into two or more sections, and wherein the thickness of the suture strand is greater than the thickness of the needle;
   b. inserting the needle through tissue surrounding the sternal bone, thereby creating a needle track through said tissue;
   c. emplacing the radially compressible suture strand in the needle track in a manner that (1) forms a loop around the sternal bone which has been divided, and (2) causes the radially compressible suture strand to exert gentle pressure against surrounding tissue, to minimize bleeding;
   d. forming a plurality of such loops around the sternal bone; and,
   e. securing the loops at a level of tension suitable for maintaining closure and healing of the sternal bone segments.

2. The method of claim 1 wherein the suture strand is made of a flexible material having a hollow tubular shape.

3. The method of claim 1 wherein the suture strand is made of an outer layer of compressible material which surrounds at least one inner reinforcing strand.

4. The method of claim 1 wherein the suture strand is coated with a compound that can reduce friction as the suture strand is emplaced in the needle track.

5. The method of claim 1 wherein the securing step further comprises:
   a. providing a suture strand fastener device comprising a cylinder, a plunger which is slidably enclosed within said cylinder, and securing means to hold the plunger in a depressed position after the plunger is depressed, wherein the plunger contains a plunger orifice through which the suture strand can pass;
   b. passing the suture strand through the orifice;

c. depressing the plunger into the cylinder in a manner which crimps the suture strand passing through the plunger orifice; and, d. engaging the securing means, to secure the plunger in a depressed position which secures the crimped suture strand passing through the plunger orifice.

6. The method of claim 5 wherein the securing step further comprises providing the suture strand fastener device with at least one extendable fixation prong which is forced into an extended position when the plunger is depressed, wherein the fixation prong when forced into an extended position reduces the likelihood of migration of the suture strand through peristernal tissue after said fixation prong has been extended.

7. A method of closing the sternum following a thoracic surgical operation which involves cutting the sternal bone into two or more divided segments, comprising the following steps:

a. using a needle having a first thickness to draw a suture strand having a second thickness into position around the divided segments of the sternal bone, wherein the needle creates a needle track through peristernal tissue, and wherein the suture strand occupies the needle track after passage of the needle; and, b. securing the suture strand in a manner which forms a secure loop which encircles the divided segments of the sternal bone, wherein the suture strand is made of a flexible radially compressible material having a thickness larger than the thickness of the needle, wherein the radial compressibility is sufficient to allow the suture strand to exert gentle pressure on tissue which encloses the needle track, thereby allowing the suture strand to help reduce bleeding generated by such tissue.

8. The method of claim 7 wherein the suture strand is made of a flexible material having a hollow tubular shape.

9. The method of claim 7 wherein the suture strand is made of an outer layer of compressible material which surrounds at least one inner reinforcing strand.

10. The method of claim 7 wherein the suture strand is coated with a compound that can reduce friction as the suture strand is pulled through bone or peristernal tissue.

11. The method of claim 7 wherein the securing step further comprises:

a. providing a suture strand fastener device comprising a cylinder, a plunger which is slidably enclosed within said cylinder, and securing means to hold the plunger in a depressed position after the plunger is depressed, wherein the plunger contains a plunger orifice through which the suture strand can pass;

b. passing the suture strand through the orifice;

c. depressing the plunger into the cylinder in a manner which crimps the suture strand passing through the plunger orifice; and, d. engaging the securing means, to secure the plunger in a depressed position which secures the crimped suture strand passing through the plunger orifice.

12. An article of manufacture useful for surgical closure of sternal bone segments following a median sternotomy, comprising:

(a) at least one strand of suture material suitable for securing closure of surgically-divided sternal bone segments without damaging the sternal bone segments during post-operative ambulation, wherein the suture strand has a diameter of at least about 2 mm and is made of a longitudinally-inelastic flexible material which will not stretch significantly in the longitudinal direction but which is radially compressible and which will attempt to expand radially after compression, thereby allowing the suture material, after emplacement in a needle track created by a needle having a diameter smaller than the suture strand, to provide gentle pressure against tissue surrounding the needle track, to minimize bleeding in such tissue; and, (b) a packaging enclosure which encloses the suture material, and which has been sealed and sterilized, and which maintains sterility of the suture strand.

13. The article of manufacture of claim 12 wherein the package also contains at least one surgical needle which is firmly coupled to the suture material, wherein the surgical needle has a thickness which is sufficiently less than the diameter of the suture strand to allow the radially compressible suture strand to exert pressure against peristernal tissue surrounding the needle track, to minimize bleeding of said tissue.

14. The article of manufacture of claim 12 wherein the package also contains at least one fastener device capable of securely gripping the suture strand in a manner that will not allow significant slippage of the suture strand during post-operative ambulation after the suture strand has been used to reapproximate sternal bones during thoracic surgery.

15. The article of manufacture of claim 14 wherein the suture strand fastener device comprises a cylinder and a plunger which is slidably enclosed within said cylinder, wherein the plunger contains an orifice through which a suture strand can pass, and wherein the suture strand passing through the orifice is crimped and held securely when the plunger is depressed, and wherein the cylinder and plunger are provided with interacting means to hold the plunger in a depressed position after the plunger is depressed to crimp the suture strand passing through said orifice.

16. The article of manufacture of claim 15, wherein the suture strand fastener device is provided with at least one extendable fixation prong which is forced into an extended position when the plunger is depressed, and wherein the fixation prong reduces the likelihood of migration of the suture strand though peristernal tissue after said fixation prong has been extended.

* * * * *